United States Patent [19]
Frei et al.

[11] Patent Number: 5,827,406
[45] Date of Patent: Oct. 27, 1998

[54] SELECTIVE PHOTOOXIDATION OF HYDROCARBONS IN ZEOLITES BY OXYGEN

[75] Inventors: Heinz Frei; Fritz Blatter; Hai Sun, all of Berkeley, Calif.

[73] Assignee: The Regents of the University of California, Oakland, Calif.

[21] Appl. No.: 710,031

[22] Filed: Sep. 11, 1996

Related U.S. Application Data

[63] Continuation of Ser. No. 382,216, Jan. 31, 1995, abandoned.

[51] Int. Cl.$^6$ .................................................. C07B 33/00
[52] U.S. Cl. ................................ 204/157.15; 204/157.6; 204/157.61; 204/158.2; 204/158.21; 204/157.93; 210/748
[58] Field of Search ........................ 204/157.15, 157.6, 204/157.61, 158.2, 158.21, 157.93; 210/748

[56] References Cited

U.S. PATENT DOCUMENTS 4,495,041  1/1985  Goldstein ............................ 204/158 R

OTHER PUBLICATIONS

Blatter et al., "Selective oxidation of propylene by $O_2$ with visible light in a zeolite," *Ctalysis Letters*, vol. 35, 1995, pp. 1–12.

Nicholas J. Turro, Photchemistry of organic molecules in microscopic reacto4rs, *Pure & Appl. Chem.*, vol. 58, No. 9, 1219–1228, (1986).

Thomas L. Pettit, et al., Photoassisted Oxygenation of Olifins: An Exchanged Zeolite as Heterogeneous Photosensitizer, *J. Phys. Chem.*, 90, 1353–1354, (1986).

Nicholas J. Turro, et al., Photochlorination of n–Alkanes Absorbed on Pentasil Zeolites, *J. Org. Chem.*, 53, 3731–3735, (1988).

V. Ramamurthy, et al., Photochemical and Photophysical Studies 9of Organic Molecules Included with Zeolites, *Acc. Chem. Res.*, 25, 299–307, (1992).

Kyung Byung Yoon, Electron– and Charge–Transfer Reactions with Zeolites, *Chem. Rev.*, 93, 321–339, (1993).

Blatter et al., *J. Phys. Chem.*, 98(50), 13403–7, 1994.
Sun et al., *J. Am. Chem. Soc.*, 116(17), 7951–2, 1994.
Blatter et al., *J. Am. Chem. Soc.* 116(5), 1812–20, 1994.
Blatter et al., *J. Am. Chem. Soc.*, 115(16), 7501–2, 1993.

*Primary Examiner*—Cecilia J. Tsang
*Assistant Examiner*—C. Delacroix-Muriheid
*Attorney, Agent, or Firm*—Hana Verny

[57] ABSTRACT

A selective photooxidation process for the conversion of hydrocarbon molecules to partially oxygenated derivatives, which comprises the steps of adsorbing a hydrocarbon and oxygen onto a dehydrated zeolite support matrix to form a hydrocarbon-oxygen contact pair, and subsequently exposing the hydrocarbon-oxygen contact pair to visible light, thereby forming a partially oxygenated derivative.

20 Claims, No Drawings

SELECTIVE PHOTOOXIDATION OF HYDROCARBONS IN ZEOLITES BY OXYGEN

This is a continuation of application of Ser. No. 08/382,216 filed Jan. 31, 1995, now abandoned.

BACKGROUND OF THE INVENTION

1. Field of the Invention

This invention relates to a photochemical process for the selective oxidation of hydrocarbon molecules adsorbed onto inert support matrices. More particularly, the invention is concerned with a highly selective method for the visible light-induced molecular oxidation of small hydrocarbon species supported on zeolite compositions to permit the synthesis of specific oxidation products.

2. Brief Description of the Related Art

A majority of the organic building blocks and intermediates required for the manufacture of plastics and other synthetic materials are produced by the partial oxidation of small hydrocarbon molecules such as toluene, propylene, isobutane and propane. Unfortunately, typical oxidizing agents which are used, such as organic hydroperoxides and hydrogen peroxide ($H_2O_2$), are expensive when used on production scales. In addition, many current industrial oxidation processes create environmental problems due to the often accompanying formation of undesirable and non-useful byproducts. Commercial-scale purification processes also tend to be non-energy efficient and therefore drive up costs further. An additional problem associated with current thermal oxidation reactions by $O_2$ (autoxidations), particularly those involving small hydrocarbons, is that these processes exhibit very low selectivity and can only be conducted with low conversions. To overcome this problem, many $O_2$-autoxidation processes used to make commodity chemicals require specialized techniques, such as transition metal catalysts or gas phase reactions, either of which can add additional expense and processing steps.

Further complicating this picture is the number of reactive intermediates which can form. The chain reaction leading to the primary hydroperoxide product can be diverted by termination steps, resulting in the formation of oxy radicals. These highly reactive species can undergo competing reactions that are very difficult to control. Depending on the starting material used, the result can be a multitude of products such as alcohols, carbonyl compounds and epoxides. Each of these products necessitate additional steps to isolate the desired hydroperoxide and ultimately introduce added expense to the process. Furthermore, alcohols, epoxides and carbonyls are more easily oxidized by $O_2$ under thermal conditions than the parent hydrocarbon. Because of the low chemo- or regioselectivity of these secondary reactions, and because formation of the most stable oxidation product, $CO_2$, cannot be prevented in many cases, present methods for conversions involving oxidations by $O_2$ have to be kept as low as a few percent. A major challenge in the field of hydrocarbon-$O_2$ chemistry, therefore, has been to find more economical and environmentally compatible reaction pathways that afford partially oxygenated derivatives with high selectivity and high conversions.

In light of the foregoing problems, there has been great interest in the use of molecular oxygen naturally present in the atmosphere as an oxidation source. The virtually unlimited supply of this resource has underscored its use and its desirability as the most inexpensive and environmentally benign oxidant available. The challenge to achieving oxidation to specific products has, however, proved difficult to realize and has been the subject of much research. Although synthesis of small molecules in gaseous or solution phase tends not to afford much selectivity or the ability to control product ratios, a number of researchers have nonetheless turned their attention towards chemistry on solid supports at low temperatures induced by light in order to gain greater control of reaction processes. Supports of choice tended to be matrices at cryogenic temperatures, molecular sieves or zeolites. Zeolites, widely used as molecular sieves, catalysts, ion exchange media and detergent builders, are widely accepted from an environmental standpoint. Until fairly recently, however, zeolites were studied principally for their role in catalytic reactions such as petroleum refining processes. While catalysts have traditionally been of interest for their ability to alter the speed of chemical reactions and not necessarily their selectivity, a number of workers have fairly recently employed zeolites to investigate various parameters relating to photochemical reactions. However, very little work involving synthetic photochemistry has been done in support matrices.

In one study by Turro, *Pure & Appl. Chem.*, Vol. 58, No. 9, pp. 1219–1228 (1986), the photolysis of dibenzyl ketone and its derivatives was investigated using representative faujasite- and pentasil-type zeolites. The goal was to learn what role the zeolite might play in controlling the reactions of organic molecules adsorbed on internal and external zeolite surfaces. Due to the "sieving" characteristics of zeolites to selectively adsorb molecules based on size and shape, it was anticipated that the course of chemical reactions might be dominated by the zeolite structural environment. Aside from the existence of size and shape selectivities, the presence of geminate triplet radical pairs generated under the reaction conditions employed accounted for the variety of reaction products observed. In short, this work explored various zeolites as reaction supports and concluded that unique size and shape characteristics of zeolite frameworks could control secondary processes occurring after a primary photochemical process. The article provided no insight into whether or how oxidation reactions within zeolite frameworks could be controlled in order to generate specific products.

In 1986, Petit, et al., report the use of zeolites in the generation of singlet oxygen species in *J. Phys. Chem.*, 90, 1353 (1986). However, the zeolites were used to generate heterogeneous photosensitizers which were used in solution. Dutta, et al., in *J. Phys. Chem.* 96, 4087 (1991) studied the hydrogen bonding donor and acceptor ability of $Na^+$ exchanged fugasites, and found that they were comparable to strong polar hydroxylic solvents. It was determined that the silica to aluminum (Si/Al) ratio of the zeolite framework determined the acid-base character of the zeolite. Dutta further determined that electrostatric (dielectric) effects of the zeolite did not appear to be important in stabilizing zwitterionic (charge-transfer) structures, and did not pursue electrostatic effects further.

In a 1988 article, Turro, et al., in *J. Org. Chem.*, 53 (16), 3731 (1988), report the use of zeolites for photochemical transformations of n-alkane species, but the reactions studied were chlorinations, and there is no mention of the technique for oxidations.

In an article which appeared in 1992, Ramamurthy, et al., in *Acc. Chem. Res.* 25, (1992), 299–307, address the subject of controlling photophysical and photochemical behavior of guest molecules within zeolites, and discuss mostly pentasils and some faujasites. However, Ramamurthy focuses primarily on oligomerization and polymerization reactions, and states that size matching between the host and the guest is essential for achieving maximum selectivity. The zeolites used in this study were activated by heating them in an aerated furnace at 500° C. for twelve hours. In perhaps a related study which appeared the same year in *Chimia*, 46 (1992) 359–376), Ramamurthy studied the phosphorescence of a variety of large molecular aromatic species in pentasils and faujasites. Photochemically induced oligomerizations and polymerizations were also studied, but these reactions were generally carried out at cryogenic temperatures using excitation UV light (wavelengths below 400 nm). While details on zeolite preparation are not readily ascertainable, this work makes the point that the use of reaction cavities of the proper configuration, with respect to free volume and reaction cavity size, are key factors in obtaining high product selectivity. Oxidation reactions are neither mentioned nor suggested, nor is there any mention of stabilization of charge-transfer states.

A more recent review by Yoon, in *Chem. Rev.*, 93 (1993), 321–339, discloses the formation of charge-transfer complexes in pentasil and faujasite zeolites, but this article uses zeolite slurries formed when partially dehydrated zeolites were combined with a variety of solvents containing aromatic molecules. While superoxide ($O_2^-$)-containing species were isolated and investigated in one part of the study, there was no mention of light-induced photooxidation reactions nor any discussion as to the selectivity of those reactions studied. In fact, the only mention of irradiation of zeolites was the exposure of alkaline earth metal ion exchanged zeolites that contained adsorbed substrates to high energy gamma- or X-rays.

In summary, none of the foregoing references, nor any combination thereof, teaches, discloses or suggests a process by which oxidation reactions, in particular photooxidation reactions involving atmospheric oxygen, can be carried out in an economical and environmentally viable manner. Furthermore, none of the foregoing teach, disclose or suggest techniques for the formation of highly useful and industrially desirable photooxidation products generated with high selectivities, without employing solutions, cryogenic inert gas matrices, gas phase reactions or catalysts, or requiring the input of high energy to initiate the process.

It is therefore an object of this invention to provide an economical and convenient oxidation method for the selective production of useful and industrially significant molecules.

It is a further object of this invention to provide a convenient method for the oxidation of small hydrocarbon molecules adsorbed onto a solid support.

It is an additional object of this invention to provide a low energy process for the photooxidation of small hydrocarbon molecules.

It is yet another object of this invention to provide a photooxidation process that exhibits a high degree of selectivity at high conversion.

SUMMARY OF THE INVENTION

The instant invention is based on the discovery that small hydrocarbon molecules can be selectively oxidized using molecular oxygen and visible light upon incorporation of the reactants into the porous structure of an inert polar matrix such as a zeolite. It was further discovered that when supported oxygen-containing charge-transfer complexes are irradiated with electromagnetic energy in the visible range of the spectrum, photooxidation products of industrial importance may be obtained which exhibit remarkably high degrees of selectivities.

DEFINITIONS

In this document, use shall be made of the following phrases and terms of art, which have the meanings as indicated below.

As used herein, the term "conversion" refers to the amount of starting hydrocarbon material which has undergone photooxidation and has reacted to form a new product or products. As such, the term is a relational one which compares the amount of unreacted starting material remaining after photooxidation with the total amount of starting material initially present to indicate the degree of completion of the photooxidation process under a certain set of conditions.

As used herein, the phrase "dark reaction" is used to refer to a spontaneous reaction that occurs in the absence of visible light. "Thermal reaction" as used herein is also understood to be synonymous with "dark reaction."

The term "photooxidation" or the phrases "oxidation by visible light" or "treatment by visible light" as used herein refers to the exposure of one or more substances to energy in the visible range of the electromagnetic spectrum. Electromagnetic energy is propagated through space or through material media in the form of an advancing disturbances in electric and magnetic fields which exist in space or in the media. The visible region of the electromagnetic spectrum is a rather arbitrarily defined subportion of the continuum of wavelengths which comprise electromagnetic energy, and generally refers to light which has a wavelength characteristically found in the range of 4000 to approximately 7000 angstroms (Å), or approximately 400 to approximately 700 nanometers (nm). Red light refers to electromagnetic energy or photons having wavelengths in the range from approximately 6470 to 7000 Å (647 to 700 nm), while blue light, which is found at the opposite end of the visible spectrum, refers to electromagnetic energy or photons having wavelengths in the range from approximately 4240 to 4912 Å (424 to 491 nm). The terms "oxidation" or "photooxidation", when taken alone or in combination with the words "treatment", "exposure", "irradiation" or "radiation" are understood to be generally synonymous within this context.

As used herein, the term "selective" is used to characterize a reaction or process, and is descriptive of the final product or products generated. That a particular reaction or process is "selective" means that only one reaction intermediate is formed at more than 95%, and that once an isolable initial product has been formed, there is no further reaction or decomposition of that species under the initial reaction conditions.

As used herein, "supercage" or, alternately, "nanocage" are terms used to describe the topological structure of zeolites or support materials in reference to the rather large spherical cavities which are generated by the intersection of interconnected three-dimensional networks characteristic of these materials.

DETAILED DESCRIPTION OF THE INVENTION

Unless specifically indicated otherwise, all amounts given in the text and the examples which follow are understood to be modified by the term "about", and those figures expressed in terms of percent (%) are understood to refer to weight-percent.

The present invention is concerned with the selective photooxidation of hydrocarbon molecules in zeolite matrices by molecular oxygen via the use of electromagnetic radiation in the visible region of the spectrum. One unique aspect of this invention is the discovery that strong electrostatic fields present inside zeolite matrices play a crucial role in the ability of the matrix to stabilize hydrocarbon. $O_2$ species, and subsequently enable photooxidation reactions to be initiated using relatively low power light of visible wavelengths. While zeolites are well known primarily for their importance as catalysts and for providing catalytic supports in the petroleum industry, Application known of no prior work that teaches or suggests that strong electrostatic fields found inside zeolite cages can be used to stabilize charge-transfer states of coordinated hydrocarbon-oxygen moieties, nor that relatively low-energy oxidation reactions could be subsequently initiated using visible light. Further, to Applicants knowledge, the work described herein is unique in that it represents the first instance in which selective photooxidation reactions may be conducted directly by taking advantage of the stabilization of a hydrocarbon. $O_2$ contact pair by a zeolite moiety, as compared to solution or gas phase environments, or the need for catalysts. And still furthermore, the reactions of the present invention are remarkable in that they exhibit a high degree of product selectivity, and have been found to generate highly desirable and extremely useful oxidation products.

Remarkably, Applicants have determined that when zeolites are prepared according to the method of the present invention, it is possible to access new, lower energy routes for oxidation reactions that involve initiation by visible light. Applicants discovered that upon the introduction of hydrocarbons and oxygen into a suitably prepared zeolite support, a shift in absorption bands towards lower energy was detected. The absorption band normally found in the UV region of the spectrum becomes altered, and an absorption band extending from the UV to the visible region can be observed. This shift has been determined to reflect an astonishingly large stabilization of approximately 1.5 electron volts. (See Blatter, et al., *J. Amer. Chem. Soc.*, 1993, 115, 7501, which is incorporated herein by reference.) This represents a stabilization of several hundred nanometers, or approximately ten thousand wave numbers ($cm^{-1}$). Normally, hydrocarbon molecules in solution exhibit characteristic absorption bands in the UV region of the electromagnetic spectrum. To Applicants' knowledge, no such shift from the UV to lower energy has been previously taught or suggested for hydrocarbons and oxygen alone in the gas phase, nor has a shift to longer wavelengths been reported in the prior-art for zeolites prepared by conventional routes.

Without being bound by any particular theory, Applicants believe that this relatively large shift may be attributed to the existence of a stabilized excitation state for the hydrocarbon. $O_2$ charge-transfer moiety. Following a number of experiments, Applicants have been able to rule out several alternative explanations for this surprisingly large stabilization in favor of a charge-transfer intermediate. For one thing, excitation of an $O_2$-enhanced triplet absorption of 2,3-dimethyl-2-butene (DMB) was ruled out because it is known that the lowest triplet state of the alkene lies in the UV region. (See Murov, S. L., *Handbook of Photochemistry*; Marcel Dekker, New York 1974.) Excitation of $(O_2)_2$ cooperative absorptions in the visible spectral range are not likely because these species exhibit well-established discrete absorption bands. (See Landau, et al., *Spectrochim. Acta*, 1962, 218, 1–19.) Further, as product growth ceased when oxygen was selectively removed by evacuation, the intermediate complex must be one that is able to undergo reversible formation. A state involving hydrocarbon-host matrix interaction can thus be ruled out. A singlet $O_2$ species was also eliminated from consideration when it was shown that use of the much less polar high-silica faujasite, with a ratio of Si to Al greater than 100 (Si:Al >100:1), resulted in the formation of a higher percentage of acetone being formed. A less polar excitation state for acetone is consistent with a charge-transfer reaction mechanism, and explains the observed difference in product ratios realized upon using a zeolite with a lower electrostatic field. Moreover, hydrocarbons which are known not to react with singlet oxygen were found to react photochemically with $O_2$ in the support matrices. Applicants therefore suggest, without being bound by any particular theory, that a key step in the process of the present invention is charge separation followed by proton transfer from the hydrocarbon radical cation to $O_2^-$ to give rise to a hydrocarbon radical, and a OOH radical.

Further support for the existence of stabilization of hydrocarbon-$O_2$ charge-transfer absorptions comes from the observation that the energy of the long wavelength absorption depends on the ionization potential of the hydrocarbon. It has surprisingly been observed that a shift of more than 10 000 $cm^{-1}$ (300 nm) occurs when DMB and molecular oxygen are enclosed within the nanocages of zeolite NaY prior to irradiation with visible light. The onset of the DMB-oxygen charge-transfer absorption is at 760 nm. The onset of the propylene-oxygen charge-transfer absorption in zeolite NaY is at much higher energy, 450 nm, reflecting the higher ionization potential of propylene compared to DMB by 1.4 eV. (See CRC *Handbook of Chemistry and Physics*, 53rd ed.; The Chemical Rubber Co.; Cleveland, 1972; p. E-62.) Increasing the electrostatic field of the zeolite by substituting BaY for NaY shifts the onset of the propylene-oxygen absorption from 450 to 520 nm. Applicants believe that these observations strongly support the stabilization of the excited hydrocarbon-oxygen charge-transfer state by the electrostatic field as being responsible for the observed red shift in zeolites. The existence of these approximately 10 000 $cm^{-1}$ and 11 000 $cm^{-1}$ shifts in absorption bands upon formation of hydrocarbon. $O_2$ contact pairs, to Applicants' knowledge, have neither been proposed nor reported previously.

On the contrary, red shifts of charge-transfer bands from solution or for high-pressure $O_2$ gas environments that have been reported for organic systems typically lie in the 10–30 nm range, such as those for aromatic (donor)-pyridinium (acceptor) complexes. (See Yoon, K. B., *Chem. Rev.*, 1993, 93, 321–339 and references cited therein.) Similarly, changing the polarity of the organic solvent over a wide range has little effect on the alkene.$O_2$ charge-transfer absorption. See Blatter, F., and Frei, H., *J. Am. Chem. Soc.*, 1994, 116 (5), 1812, and further citations therein. In passing, it may be noted that one report of a charge-transfer moiety stabilized on solid-$O_2$ recently appeared (see S. Hashimoto, et al., *J. Phys. Chem.*, 1987, 91, 1347) for which stabilization larger than 30 nm was reported. However, Applicants have been unable to detect any reaction in a solid $O_2$ matrix using visible light.

Applicants have further determined that photooxidation reactions conducted according to the method of the present invention are surprisingly useful and beneficial, in that the processes are highly selective, and result in the formation of very desirable products via convenient pathways. For example, it is known in the prior art that in gas, solution and solid $O_2$ matrices, photoreactions can only be induced by ultraviolet (UV) light. UV-induced reactions are known to be intrinsically non-selective and indeed, as a consequence, a mixture of products are obtained upon UV irradiation. By contrast, the photooxidation of zeolite-supported hydrocarbon.$O_2$ complexes of the present invention, which complexes rise to charge-transfer bands in the visible range of the electromagnetic spectrum, yield only selected products. One possible explanation for this difference in selectivities is that gas, solution and solid $O_2$ matrices are each incapable of stabilizing the hydrocarbon. $O_2$ charge-transfer state. The ability of the zeolites of the present invention to stabilize charge-transfer states to lower energy in general, and hydrocarbon. $O_2$ charge-transfer states in particular, is therefore a distinguishing feature of the present invention.

According to one method of the present invention, photooxidation reactions are initiated when photons of visible light are made to impinge upon zeolite-bound $O_2$-containing contact pairs. Once the initial oxidation product has been formed, subsequent impinging photons have been found to cause no further chemical reaction. That is, continuous irradiation of the initial product or products formed under the initial reaction conditions causes no further breakdown or decomposition. The tremendous selectivity of the zeolite-supported reactions of the present invention are further evidenced by the fact that formation of the most stable oxidation product, $CO_2$, can be completely avoided. As a result, unlike conventional aut processes where conversions have to be kept low—on the order of a few percent, to avoid excessive $CO_2$ formation and other byproduct formation—no such restriction is necessary with the instant invention. There is no $CO_2$ formed in any of the photooxidation reactions of the current invention, whatsoever. The remarkable selectivities observed from the light-induced reactions of the present invention could not have been predicted a priori based solely on the visible wavelength shifts of the hydrocarbon.$O_2$ charge transfer bands.

In general, the photooxidation reactions of the present invention yield the hydroperoxide (—$O_2H$) containing moiety corresponding to the initial starting hydrocarbon at better than 95% selectivity relative to any or all other reaction products formed. In fact, selectivities are generally on the order of 97% or better, and exhibit only minor variation with temperatures over a broad range. For example, in the case of propylene in BaY, selectivity at 173° K (–100° C.) was approximately 99.5%, while selectivity at room temperature was approximately 98%. It is therefore said that the reactions of the present invention are selective for hydroperoxide formation. An illustrative example may be given in one embodiment of the present invention for toluene, which, upon undergoing selective photooxidation, yielded benzaldehyde as the exclusive product, which comes from the decomposition of the benzyl hydroperoxide which is transitorily formed. There was no further oxidation to benzoic acid. Thermal reactions and rearrangements may play a role in the final product distribution in certain instances, however, the initially formed hydroperoxide exhibits temperature sensitivity in many cases. While different product distributions are therefore observed at different temperatures, it should be remembered that these product branchings can be manipulated by the choice of experimental conditions, such as temperature and hydrocarbon concentrations. Note that different product distributions do not mean that the selectivity of the initially formed hydroperoxide product has changed, but merely that there has been a subsequent manipulation of the hydroperoxide. Carbon dioxide is not formed in any of the photooxidation reactions.

Zeolites are crystalline aluminosilicate minerals with the general formula $$M_x[(AlO_4)_x(SiO_4)_y]\cdot nH_2O$$

which gives rise to a structure based on a three dimensional network of $[AlO_4]^{5-}$ and $[SiO_4]_{4-}$ tetra linked to each other via doubly bridging oxygen atoms. The network of alumina and silica tetrahedra give rise to the porous nature of zeolite structures, making zeolites widely used as sorbents, ion exchange media, catalysts and catalyst supports. Counter ions, such as cations, which are represented by the letter M in the foregoing generalized equation, must be present in order to compensate for the otherwise excess negative charges in the zeolites. The cations are mobile and occupy various exchange sites depending upon their radius, charge, and degree of hydration. They can be replaced, to varying degrees, by exchange with other cations.

According to the present invention, M may be selected from the group comprising essentially alkali metals which includes hydrogen, lithium, sodium, and potassium, alkaline earth elements, which includes magnesium, calcium and barium, and transition elements, which may also include lanthanum. Essentially, any cation may be used. More generally, any porous solid material with molecular size cages featuring strong electrostatic fields may be used. More preferably, M is selected from the group consisting of sodium, calcium, barium, silver, lanthanum and cobalt. N in the above equation varies from about 0 (in the anhydrous form) to about 10, and x and y may vary depending upon the zeolite or solid support used. For instance, in the case of zeolite Y, x typically has a value of 56 and y typically has a value of 136.

The zeolites used in accordance with the present invention may be obtained from either natural or synthetic sources, and may contain different aluminum to silicon ratios. Various ion exchanged forms may also be used, as well as different configurations of zeolites such as zeolite A, and the more common pentasils, faujasites, and mordenites (e.g. ZSM-5, ZSM-11 and ZK-4), as well as various forms of silicates. Other types of molecular sieves such as aluminum phosphates, the so-called "AlPO's" and silica-aluminum phosphates, or "SAPO's, " as well as the new Mobil Corporation molecular sieves ("MCM's ") materials may also be used. The faujasites are preferred for the instant invention, with the synthetic Y-type faujasitic zeolites particularly preferred.

Faujasites are zeolite with cavities consisting of a three-dimensional network of molecular cages having a diameter of approximately 13 angstroms (Å), interconnected by window openings having a diameter of approximately 8 angstroms (Å). Faujasites may exhibit a variable ratio of silicon to aluminum (Si/Al). High-silica faujasite (HSF) generally has a ratio of Si to Al (Si/Al) greater than 100, with little or no univalent cations present in the nanocages that comprise the zeolite structures. That is, Si and Al cations balance the negatively charged oxygen atoms, such that there is generally less than one $Na^+$ per nanocage, and often there may be no $Na^+$ present. The result is that high silica faujasite has a lower electrostatic field, which is estimated to be approximately 0.1 volts per angstrom (V/Å). Y-type faujasites, by contrast, generally compensate the negative charge introduced by the aluminum atoms of the zeolite cage walls with cations other than Si or Al to a larger extent. In faujasite NaY, for example, the Si/Al ratio is approximately 2.5, and there are seven $Na^+$ per nanocage (as many as 56 Na ions per unit cell). Electrostatic charges for NaY and other substituted zeolites are therefore much higher. The electrostatic field strengths for CaY, BaY and NaY have been determined to be 0.3 V/Å, 0.5 V/Å AND 0.2 V/Å, respectively. Although each of the X-, Y- and HSF-type faujasites may be used for the photooxidation processes of the current invention, X- and Y-type faujasites are preferred over HSF-type faujasites because of the higher electrostatic fields inside the nanocages. Other zeolites or solid supports that have internal electrostatic fields of similar strengths to the faujasite zeolites used in the present work may also be used in accordance with the teaching of the present invention. Essentially, electrostatic fields of strengths of at least 0.15 V/Å may be used, as determined by induced infrared absorption of nitrogen for measurements of electrostatic fields within the nanocages. Values above about 0.2 V/Å for electrostatic field potentials are generally preferred.

An important feature of the complexes used in the present invention is that the electrostatic fields present in the zeolites can be fine-tuned by the choice of the alkali, alkaline earth or transition element ions selected for incorporation into the nanocages. Combinations of counter ions may also be possible. Enhancement of the electrostatic field within the zeolite nanocages by substitution of Na+ by a smaller cation such as $Li^+$, or by a bivalent cation such as $Mg^{2+}$ in place of $Ba^{2+}$, for example, should also permit access to visible light-induced oxygenation reactions of additional small hydrocarbons. The electrostatic charges that are subsequently generated within the zeolite nanocages may thus cover a wide range, and can therefore be used to stabilize species towards oxidation reactions over a wide range of ionization potentials.

One key feature of the present invention is that the preparation of zeolites which are used as supports in the photooxidation reactions is remarkably straightforward. The zeolites are simply dehydrated with mild heat treatment under vacuum to drive off adsorbed water. Typically, temperatures of 100° C. to 500° C. may be used. More preferably, temperatures between 150° C. to 250°C. may be used. According to one method of the invention, zeolites are preferably heated under vacuum at about 200° C. After heat treatment, approximately 99% of the adsorbed water has been removed. In one method of the invention, the zeolites are heated for approximately 12 to 16 hours. Heat treating the zeolites under vacuum, while simultaneously avoiding prolonged heating, prevents the generation or activation of acidic sites within the zeolites. Conventional methods for the preparation of zeolites currently in use, most notably in petroleum refining, involve heat treatment for prolonged periods, usually at higher temperatures, in the presence of hydrogen or nitrogen gas, or under other conditions conducive to the generation of acidic sites in the matrices. The absence of Lewis acid sites due to the mild treatment of the zeolites may be crucial to the high selectivites found in the processes of the present invention. The light-induced photooxidation reactions described herein are appropriate for all hydrocarbon starting materials, with relatively few restrictions. One important consideration of the current invention, however, is the ionization potential of the hydrocarbon used. A wide variety of hydrocarbon molecules may be successfully oxidized via visible light-induced photooxidation, provided that the zeolite is capable of stabilizing the hydrocarbon. $O_2$ contact pair which is formed within the zeolite. In this respect, it is essential that ionization potential of the hydrocarbon give rise to a charge-transfer state for the adsorbed hydrocarbon. $O_2$ moiety which lies within the visible range, by virtue of the stabilization by the electrostatic charges associated with the zeolite nanocage. If the ionization potential of the starting material is too high, such that the charge-transfer of the $O_2$-bound contact pair lies outside the range of the visible spectrum, photooxidation according to the process of the present invention will not occur. This applies, in particular, in the case of alkenes. However, whether or not reaction will take place also depends on the reaction mechanism typical for these type of oxidations. It is required that alkenes have a hydrogen in the alpha position to the double bond. For example, no reaction was observed upon photolysis of 3,3-dimethyl-1-butene with oxygen adsorbed onto NaY zeolite, regardless of the visible wavelength used. The ionization potential for 3,3-dimethyl-1-butene (9.5 eV) however, was too high for stabilization within the NaY zeolite used, and in addition, the molecule lacks an alpha-hydrogen atom. In the case of isobutane, photooxidation on NaY was so slow that it could barely be observed. By changing to BaY, which has a higher electrostatic field, the photooxidation of isobutane was much faster. In general, the higher the electrostatic field, the larger the stabilization of the charge-transfer state.

According to one method of the present invention, any small hydrocarbon molecule that can be adsorbed into the nanocages of a support matrix can be used to initiate the photooxidation reactions described herein. In general, hydrocarbons having any number of atoms may be used, the only caveat being that the hydrocarbon must be able to diffuse through the nanocage openings of the support matrix. In general, hydrocarbons having as many as 100 atoms, preferably those having under 50 atoms, and most preferably those having less than approximately 30 atoms may be used. According to the present invention, the hydrocarbons may be selected from the group consisting of alkanes and substituted alkanes (including aliphatic alkanes), alkenes and substituted alkenes, and aromatics and substituted aromatics (including those with alkyl substituents). Either branched or linear forms of any of the foregoing may be used. Size constraints not withstanding, there appear to be few restrictions regarding the nature of the starting material. Essentially, any hydrocarbon molecule or substituted hydrocarbon that meets the foregoing criteria of size, ionization potential and presence of alpha-hydrogen atoms (for alkenes) may be used.

The hydrocarbon starting materials used in the oxidation processes of the present invention were generally loaded by introducing approximately 10 micro mols ($\mu$mol) of the material onto a 10 mg pellet sample of the zeolite. Given the internal zeolite parameters and the weight of the pellet used, this corresponded to a hydrocarbon concentration of approximately 1.5 molecules per nanocage. Loading of hydrocarbon materials onto support matrices may be generally kept between 0.5 to 5.0 molecules per nanocage, and more preferably, between about 1.0 and 3.0 molecules per nanocage. Temperatures during the loading process were generally kept at room temperatures, but photooxidations were also successful following loading temperatures as low as −50° C. (negative 50° C.). The small pellet size was chosen as a matter of convenience, as the pellet could subsequently be mounted in a sample cavity of a Fourier-transform infrared (FT IR) instrument to facilitate monitoring of the reactions. Other hydrocarbon starting material amounts and different zeolite configurations may also be used.

Typically, the adsorption of hydrocarbons and molecular oxygen onto the zeolites described in the present invention results in a red shift of the absorption characteristic of a hydrocarbon. $O_2$ charge-transfer moiety to the visible region. As a result, any source which can provide light within the visible spectrum may be used to initiate photooxidation. This includes light having wavelengths of about 400 nm to about 700 nm. More particularly, light between about 425 and about 675 nm may be used.

While tunable continuous wave (CW) lasers may be used to initiate the photooxidation reactions of the present invention, it is especially significant that other broad band, conventional visible light sources, filtered or even non-filtered, may be used. According to one embodiment of the present invention, for example, the blue-light irradiation of toluene. $O_2$ adsorbed onto zeolite BaY resulted in the formation of benzaldehyde as the sole reaction product. In another embodiment, trans-2-butene. $O_2$ adsorbed onto NaY and irradiated with green light gave exclusively 3-hydroperoxy-1-butene. According to yet another embodiment of the present invention, pure hydroperoxides can be obtained at $-50°$ C. (as discussed above for DMB) via treatment with $O_2$ under unfiltered visible light, without the need for additional catalysts. In addition to photooxidation reactions for $O_2$ charge-transfer complexes of 2,3-dimethyl-2-butene described earlier, and the those described above, photooxidation reactions with blue light were also observed for propylene, isobutane, and cyclohexane on a variety of supports. The products obtained were allyl hydroperoxide (AHP), tert-butyl hydroperoxide and cyclohexyl hydroperoxide, respectively. Other hydrocarbons which were also successfully photooxidized upon irradiation with blue-green light include ethyl benzene, cumene, toluene, propane, ethane and methane, etc.

Generally, it was observed that photooxidation reaction rate at a constant wavelength decreased with increasing ionization potential of the hydrocarbon starting material. However, a determining factor as to whether reaction takes place at a reasonable rate is dependent upon the mechanism of reaction. The key step is the proton transfer from the hydrocarbon radical cation to the $O_2$.

The temperatures at which the light-induced photooxidations of the present invention may be carried out can vary over a wide range. For instance, temperatures may conveniently be varied from a low of approximately $-50°$ C. to a high of approximately $30°$ C. Reactions have been conducted at temperatures as low as $173°$ K ($-100°$ C.) for propylene and as high as $80°$ C. for toluene loaded into BaY.

The visible light-induced photooxidation of hydrocarbon. $O_2$ complexes adsorbed onto zeolites according to the present invention was shown to be a rather efficient process. For example, the quantum efficiency for the treatment of toluene. $O_2$ on CaY with blue light at 488 nm enabled estimation of the quantum efficiency of the reaction to be on the order of 10%. (See Sun, H., et al., *J. Am. Chem. Soc.*, 1994, 116, 795 1, which is incorporated herein by reference.) These is a rather high quantum yield for the conversion of toluene to benzaldehyde, and represents a distinct improvement over prior art processes which are currently in use. Commercial processes for the production of benzaldehyde in solution proceed by a costly $Co^{3+}$-catalyzed route, and suffer from the disadvantage that continued oxidation of the aldehyde to benzoic acid takes place. The quantum efficiency for the photooxidation of propylene in zeolite BaY at 488 nm to give exclusively allyl hydroperoxide (AHP) was even more efficient. In this latter instance, the quantum efficiency was estimated to be approximately 20%. (See generally F. Blatter, et al., *J. Phys. Chem.*, 98, 13405 (1994), which is incorporated herein by reference.) These rather high quantum yields are crucial for the usefulness of the described photooxidation reactions of the present invention.

The present invention will be further understood by reference to the following specific Examples which describe and embody advantages of the selective photooxidation of hydrocarbons in zeolites by oxygen. As will be readily apparent to one skilled in the relevant art, these Examples are illustrative of various parameters of the present invention, and in no way limit its scope.

EXAMPLES

Unless indicated otherwise, all percentages given are expressed in terms of weight percent. Photochemical conversions are expressed in terms of the percent of reactant molecules exposed to light. Thermal conversions are expressed in terms of the percent of total reactant that was initially loaded into the zeolite. Preparation of the zeolites for loading with hydrocarbons involved dehydrating the desired zeolite at $200°$ C. for 12 to 16 hours under vacuum. Samples were generally loaded at room temperature by introducing approximately 10 micro mols ($\mu$mol) of a hydrocarbon onto a 10 mg pellet of the zeolite. This corresponded to a hydrocarbon concentration of approximately 1.5 molecules per nanocage. The zeolites were mounted inside a miniature infrared vacuum cell into which oxygen at 500 Torr (0.66 atm) could then be introduced, unless indicated otherwise. The vacuum cell, in turn, was mounted in an infrared/optical cryostat which permitted variation of the temperature of the zeolite matrix from $77°$ K to $200°$ C. For excitation by visible light, broad band sources within the same wavelength region, i.e., blue light, red light, etc., can also be used. Where laser light sources were used, the upper limit for laser heating effects was determined to be approximately 10 degrees. (See H. Sun, et al. *J. Am. Chem. Soc.*, 1994, 116, 7951–7952, which is incorporated herein by reference, and references cited therein.) Further information regarding sample preparation and details of spectral analyses have been previously published, and are incorporated herein by reference. See Blatter, F. and Frei, H., *J. Am Chem Soc.*, 1994, 115 (5), 1812.

Example 1

The material to be photooxidized, 2,3-dimethyl-2-butene (DMB), was loaded from the gas phase into a dehydrated NaY zeolite wafer at $-50°$ C. (negative $50°$ C.). Irradiation was carried out by photolysis at 633 nm using a 300 mW $cm^{-2}$ light source with $3.5 \times 10^{21}$ photons at temperatures ranging from about $-50°$ C. to about $30°$ C. for two hours, during which time all absorption bands for DMB decreased. The only products obtained from the photolysis reaction were 2,3-dimethyl-3-hydroperoxo-1-butene (greater than 90% selectivity) and acetone (less than 4% selectivity). At $-50°$ C., less than 1% acetone was produced. This value changed to approximately 3% at room temperature. The product ratio of acetone to hydroperoxide was generally less than 0.01 for the low-temperature reactions studied.

Example 2

This Example is similar to Example 1, except that unfiltered light from a tungsten source was used. Irradiation gave the same product growth within 5% of the yields obtained in Example 1A. At room temperature, acetone was again produced in approximately 3% yield.

Example 3 and 4

These Examples are similar to that in Example 1, except that photolysis was carried out at 514 nm (Example 3) and 458 nm (Example 4) for 30 minutes at $-50°$ C. using a 400 mW $cm^{-2}$ light source. purpose for these Examples was to learn what effect changing the wavelength of the light source would have on the oxidation. Upon employing this higher energy of irradiation, slightly more acetone was generated, with the final yields of 2,3-dimethyl-3-hydroperoxo-1-butene (greater than 90% conversion) similar to those reported for the hydroperoxide in Examples 1 and 2 above. At −50° C. and either 514 or 458 nm, selectivity for hydroperoxide was approximately 98%, and selectivity for acetone was approximately 2%.

Growth of the hydroperoxide absorption band at 1365 cm$^{-1}$ was followed for the oxidation reactions described in Examples 1, 2, 3 and 4. Comparison of the results thus obtained reveals that the product ratio of acetone to hydroperoxide increased with higher photon energies. The same change in the acetone/hydroperoxide branching ratio was reproduced in tungsten lamp experiments when the photolysis wavelength was increased. This demonstrates that alkene +O$_2$ photochemistry can readily be achieved with the emission of a conventional broad-band lamp, or with light from natural sources. The advantage of using a tunable laser is that it permits selective manipulation of product ratios, as well as elucidation of the wavelength dependence of the photochemistry.

Example 5

Irradiation of DMB and oxygen adsorbed onto zeolite NaY at room temperature with light at 514 nm (400 mW cm$^{-2}$) gave 2,3-dimethyl-3-hydroperoxy 1-butene and acetone as the only photochemical products. These products were obtained with selectivities in the amounts of approximately 96% and 3%, respectively.

Example 6

Toluene was loaded from the gas phase into a sample of dehydrated zeolite BaY, which in turn was prepared by ion exchange of NaY in a 0.5M BaCl$_2$ solution. Inductively-coupled plasma atomic emission spectroscopy showed that 95% of the Na$^+$ ions had been replaced by Ba$^{2+}$. (See H. Sun, et al., *J Am. Chem. Soc.*, 1994, 116, 7951–7952). Oxygen was then introduced into the matrix at 500 Torr (approximately 0.66 atm) as described in Example 1 above. Several different visible light sources were then used to initiate photooxidation of the toluene. O$_2$ complex at temperatures from as low as −50° C. to a high of 80° C., although these reactions were typically carried out at ambient temperatures. A tungsten source (wavelengths greater than 390 nm) with a Corning filter No. 3–75 as well as blue or green emissions from a continuous wave (CW) dye laser or an argon (Ar) ion laser were used to produce light at 400 mW/cm$^2$ power. Upon irradiation for three hours, benzaldehyde was identified as the exclusive final oxidation product. Interestingly, increasing the oxygen partial pressure from 500 Torr (0.66 atm) to 4000 Torr (8 atm) enhanced the reaction rate by a factor of approximately 5.

Example 7

In this Example, toluene and oxygen were supported on dehydrated zeolite CaY in place of the BaY used in Example 6. Preparation of the CaY was carried out in a manner analogous to the preparation for BaY in Example 6, with ion exchange of NaY carried out in a 0.5M CaCl$_2$ solution. Subsequent analysis of the CaY revealed that 98% of the Na$^+$ sites had been replaced by Ca$^{2+}$. Photooxidation of the toluene. O$_2$ zeolite moiety was initiated by visible light at wavelengths below 590 nm. At room temperature, selectivity was 100% at more than 50% conversion, as benzaldehyde was the only product isolated.

Example 8

In Example 8, DMB was adsorbed onto dehydrated high-silica faujasite (Si:Al ratio greater than 100:1). Oxygen was loaded at a pressure of 500 Torr, and the photooxidation was carried out at −50° C. at several wavelengths. The maximum wavelength at which reaction could be induced was 600 nm. Upon irradiation at 514 nm (400 mW cm$^{-2}$ for 1 hour), it was learned that the branching ratio of acetone/hydroperoxide is shifted strongly in favor of acetone in the presence of high-silica faujasite as compared to the distribution in NaY (see Example 2A for comparison). High-silica faujasite (HSF) is much less polar than NaY, and use of HSF thus favors the product, acetone in the present instance, with the less polar transition state. These results further indicate that the ratio of products obtained via photooxidation in supported zeolites may be selectively varied depending upon the electrostatic properties of the zeolite nanocage used.

Example 9

Dehydrated NaY was loaded with trans-2-butene and oxygen at −50° C. Irradiation below 600 nm (514 nm, 400 mW cm$^{-2}$) for 1 hr gave rise to $CH_2=CH-CH(CH_3)-OOH$ (3-hydroperoxy-1-butene) as the exclusive photooxidation product. Selectivity was greater than 99%, and overall conversion was greater than 75%. Photolysis could be conducted for up to 10 hours with no accompanying loss of selectivity.

After photolysis, the hydroperoxide-containing zeolite was warmed up to room temperature. Upon warming, some thermal decomposition of 3-hydroperoxy- 1-butene was observed to also yield s-trans and s-cis conformers of methyl vinyl ketone.

Example 10

Irradiation of cis-2-butene and O$^2$ loaded onto dehydrated NaY at −50° C. yielded $CH_2=CH-CH(CH_3)-OOH$ (3-hydroperoxy- 1-butene). The product is the same as that obtained when trans-2-butene is used as the starting material, as in Example 9. Selectivity (above 99%) and conversion (above 75%) were the same. Upon warming from −50° C. to 0° C., thermal reaction of the hydroperoxide-contained zeolite yielded methyl vinyl ketone, 3-hydroxy- 1-butene and cis-2,3-epoxybutane. Removal of excess 2-butene starting material prior to warm-up of the hydroperoxybutene-loaded matrix resulted in the formation of only the methyl vinyl ketone, with no epoxide or alcohol.

Example 11

In Example 11, both propylene and oxygen were loaded onto zeolite BaY under a variety of pressure conditions while the matrix was held at −100° C. (negative 100$^a$ C.). Pressures for propylene varied from 3 Torr (0.004 atm) to 10 Torr (0.013 atm), whereas pressures of oxygen varied from 400 Torr (0.53 atm) to 760 Torr (1 atm). The reactants were exposed to 488 nm light from either a CW Ar-ion laser or a filtered tungsten source. The major product was allyl hydroperoxide (AHP), which was formed with approximately 99.8% selectivity at greater than 75% conversion.

Upon warming of the zeolite matrix in the presence of excess propylene, one fraction of the allyl hydroperoxide decomposed to give acrolein and water, while the other fraction reacted with propylene to form allyl alcohol and propylene oxide. The final product distribution at room temperature was therefore acrolein, 37% selectivity; propylene oxide, 31% selectivity; and allyl alcohol, 31% selectivity.

Example 12

Example 12 was similar to Example 11, except that the photooxidation reaction was carried out at room temperature to yield allyl hydroperoxide with 98% selectivity as the intermediate. In addition to allyl hydroperoxide, the final products included propylene oxide and acrolein (propenal), which were produced in approximately equal amounts. Overall selectivities for all the products were allyl hydroperoxide, 38%; propylene oxide, 36%; and acrolein, 24%. Conversions were as high as 80%.

In both Examples 11 and 12, reactions leveled off after about 20% of the propylene loaded onto the zeolite had been consumed. This is due to the strong scattering of the photolysis light by the BaY pellet, which limits penetration of visible light to approximately one quarter of the zeolite volume. The conversion with respect to the propylene residing in irradiated section of BaY is therefore approximately 80%.

Example 13

Subsequent warming up of the matrix from Example 12 to room temperature, after removal of the remaining propylene and $O_2$ by evacuation, resulted in quantitative rearrangement of the allyl hydroperoxide to acrolein under elimination of water. The result of this thermal process indicates that the epoxide, like acrolein, is a secondary product formed by thermal transfer of oxygen from $CH_2=CH-CH_2OOH$ to $CH_2=CH-CH_3$, and explains why the acrolein to allyl hydroperoxide branching ratios are much larger when the photochemistry is conducted at temperatures above $-100°$ C.

Example 14

The dark or thermal reaction of isobutane adsorbed onto CaY proceeded at a reasonable rate, with overnight conversion of approximately 5%. By contrast, the light-induced reaction of isobutane (10 Torr, 0.013 atm) and oxygen (760 Torr, 1 atm) adsorbed onto zeolite CaY at temperatures as high as 0° C. to room temperature gave tert-butyl hydroperoxide as the exclusive oxidation product with selectivities for the hydroperoxide greater than 99% at room temperature. If left within the CaY zeolite matrix, the tert-butyl hydroperoxide decomposed slowly, generating acetone and methanol. The hydroperoxide product can be extracted from the zeolite through the use of a nitrogen gas stream at slightly elevated temperatures (approximately 50° C. to 80° C.).

Irradiation of the thermal reaction with blue laser light, or with a tungsten lamp at 200 mW, enhanced the rate of the initial reaction to form the hydroperoxide product by approximately a factor of 10 with no concomitant loss of selectivity. Although no photons are needed for this reaction, this Example is typical of many instances in which light can be used in tandem with the thermal reaction to enhance reaction rates.

Example 15

Thermal reaction of isobutane and oxygen adsorbed onto BaY under conditions similar to those described in Example 14 above have been observed to yield tert-butyl hydroperoxide with less than 3% conversions. The reaction could also be conducted when either a laser or tungsten lamp at wavelengths up to 540 nm and a power level of approximately 100 $mW/cm^2$ were used as light sources. Conversions of greater than 70% have been achieved at selectivities above 98%. The reactions were carried out at a variety of temperatures from 0° C. and 50° C. The hydroperoxide product can be extracted from the zeolite through the use of a nitrogen gas stream at slightly elevated temperatures (approximately 50° C. to 80° C.).

Example 16

The photooxidation of cyclohexane and $O_2$ on a variety of zeolites with blue and green light gave cyclohexyl hydroperoxide as the primary product. The zeolites used were CaY, BaY and NaY. At $-50°$ C., cyclohexyl hydroperoxide could be generated by continuous irradiation with blue light. At room temperature irradiation with blue or green light, the hydroperoxide appeared to be more stable in NaY and BaY than in CaY. The selectivity for cyclohexyl hydroperoxide was 100% at conversions greater than 80%.

With each of the different zeolites used, thermal autooxidation of cyclohexane to cyclohexyl hydroperoxide was found to take place, even at room temperature. The product of the photochemical reaction as well as the thermal reaction was therefore the same. However, visible light irradiation of the thermal reactant system enhanced the reaction rate by approximately a factor of ten. Decomposition of cyclohexyl hydroperoxide into cyclohexanone was observed to take place in all the zeolites used. The rate of decomposition was found to decrease in the order: CaY>BaY>NaY. Cyclohexyl hydroperoxide in BaY prepared according to the present invention at room temperature was found to be rather stable. Cyclohexanone was the exclusive final oxidation product in NaY and BaY.

Example 17

After loading 1–2 molecules of ethylbenzene into BaY, followed by exposure of the zeolite to 1–2 atm oxygen partial pressure, the system was irradiated with an Ar ion laser at 488 nm. The reaction can also be initiated with visible wavelengths longer than 488 nm. Irradiation of the reactant-loaded zeolite resulted in the formation of ethylbenzene hydroperoxide, which subsequently decomposed to give acetophenone and water. The selectivity for the hydroperoxide was greater than 98% at 20% conversion. The sample was irradiated for 3.3 hours at 488 nm and 500 $mW/cm^2$ power. Higher conversions can be obtained without significant loss of selectivity.

Example 18

Cumene and oxygen at 6080 Torr (8 atm) were loaded into BaY. Irradiation at 458 nm with 250 $mW/cm^2$ laser power for 2 hours resulted in the formation of cumene hydroperoxide, exclusively, with 40% conversion. Within the zeolite, cumene hydroperoxide decomposes into acetone and phenol by one pathway, and methanol and acetophenone via another pathway. The branching ratio between these two decomposition pathways was approximately one to one, and all four products were observed in every case. A ten-fold reaction increase was observed when the oxygen partial pressure was increased from 760 to 7,600 Torr (1 to 10 atm).

Example 19

Propane at 150 Torr (0.20 atm) was loaded onto a variety of dehydrated zeolite samples, after which 760 Torr (1 atm) of oxygen was subsequently added. After loading, the reactant system was left in the dark at room temperature for approximately 3 to 5 hours. While no dark reaction took place in BaY, some acetone formation was observed in CaY. The dark reaction reached an endpoint after approximately 24 hours. The conversion for the dark reaction of propane in CaY was 30%. Acetone and water are the exclusive final products of the dark reaction, as determined by in situ Fourier-transform infrared (FT-IR) spectroscopic analysis. These are decomposition products of the propane hydroperoxide which is initially formed, but has a very short half-life.

Upon irradiation at 488 nm or 514 nm (500 $mW/cm^2$) in CaY, the reaction rate of propane increased by a factor of approximately 5 compared to the dark reaction. Propane and oxygen loaded into zeolite BaY exhibit no reaction in the dark. However, when irradiated with a laser at 488 nm or 514 nm (500 mW power), the formation of acetone and water was observed. Longer visible light wavelengths may also be used. Again, these two species are the decomposition products of the initially formed propyl hydroperoxide. No other products could be detected by in situ FT-IR spectroscopy. The conversion was followed up to approximately 20%. In other zeolites or under different reaction conditions, i.e., higher oxygen pressure (10 atm) higher conversions may be reached. The light reactions can be initiated equally well by a conventional tungsten lamp when the same photon flux is used.

Example 20

A CaY zeolite sample was filled with 300 Torr (0.39 atm) partial pressure of ethane, after which 760–1320 Torr (1–2 atm) oxygen was added. Irradiation of the zeolite pellet with laser light at 458 nm resulted in the formation of acetaldehyde and water, exclusively. Longer wavelengths may also be used. Both acetaldehyde and water are decomposition products of the initially formed ethyl hydroperoxide. No other reaction products were found. The conversion was followed up to about 20%. No intrazeolite acetaldehyde polymerization was observed within the time scale of the reactions, which were generally conducted within 24–48 hours. One possible explanation for the absence of any polymerization product may be that the acetaldehyde concentration is not more than one molecule per nanocage (i.e. one mole/liter). Higher conversions and faster reaction rates may be obtained with other zeolites under different reaction conditions. This reaction is particularly significant because optimization may provide a convenient and competitive route to the Wacker process, which is currently used for the synthesis of acetaldehyde and acetic acid.

Example 21

Reaction under conditions similar to those used in Example 20 with methane as the starting hydrocarbon resulted in the formation of formaldehyde and water. No other reaction products were detected.

The foregoing description and examples describe and illustrate certain preferred embodiments of the present invention. It is not intended that the invention should be so limited, since variations and modifications thereof will be obvious to those skilled in the relevant art, all of which are within the spirit and scope of this invention. The invention is further illustrated and embodied by the claims which follow below. However, such claims do not restrict or limit the invention in any way, and obvious improvements and equivalents and alternatives, which do not depart from the spirit and scope of the invention are captured thereby.

What is claimed is:

1. A process for a selective photooxidation of alkyl benzenes, said process comprising the steps:
    (a) preparing a zeolite support matrix by dehydrating a zeolite selected from the group consisting of BaY, NaY and CaY zeolite under vacuum at temperature from about 150° to about 250° C. for about 12 to about 16 hours;
    (b) loading the alkyl benzene in amount about 10 μmol onto about a 10 mg pellet of the dehydrated zeolite support matrix having an electrostatic field about at least 0.2 V/Å, at pressure from about 1 to about 10 Torr;
    (c) introducing oxygen into the matrix of step (b) under vacuum from about 400 Torr to about 7600 Torr;
    (d) irradiating the matrix of step (c) with a visible light in yellow or red region having a wavelength of about 400 to about 590 nm at temperatures from about −100° to about 80° C. for about one to ten hours; and
    (e) producing an alkene oxidation product with about at least 80% selectivity.

2. The process of claim 1 wherein the alkyl benzene is selected from the group consisting of toluene, ethylbenzene and isopropylbenzene.

3. The process of claim 2 wherein the alkyl benzene is toluene loaded onto dehydrated BaY or CaY zeolite having the electrostatic field about 0.3–0.5 V/Å under pressure of about 500 Torr, wherein the irradiation is performed at temperature from about −50° to about 80° C. for about one to ten hours with visible blue or green light having a wavelength between 400 and 590 nm, and wherein the oxidation product is benzaldehyde.

4. The process of claim 3 wherein the zeolite is CaY and the blue-green light irradiation performed at room temperature is selectively generating benzaldehyde as a final product with at least 95% selectivity and more than 50% conversion.

5. The process of claim 4 wherein the oxidation product is formed with selectivity greater than 99% and conversion rate is higher than 75%.

6. The process of claim 2 wherein the alkyl benzene is ethylbenzene loaded onto dehydrated BaY zeolite at about room temperature at oxygen pressure about 750 Torr to about 1500 Torr, wherein said zeolite has the electrostatic field about 0.5 V/Å, wherein the irradiation is performed at room temperature for about one to about ten hours with visible light having a wavelength longer than 488 nm and wherein the oxidation product is ethylbenzene hydroperoxide and acetophenone.

7. The process of claim 6 wherein the irradiation time is more than 3 hours and wherein selectivity of the hydroperoxide is greater than 98% at 20% conversion.

8. The process of claim 2 wherein alkyl benzene is isopropylbenzene loaded onto dehydrated BaY zeolite at room temperature at oxygen pressure 6080–7600 Torr, wherein said zeolite has the electrostatic field about 0.5 V/Å, wherein the irradiation is performed at room temperature for one to ten hours with visible blue or green light of wavelength between about 400–550 nm and wherein the oxidation product is isopropylbenzene hydroperoxide and acetophenone.

9. The process of claim 8 wherein the irradiation time is two hours using a light having a wavelength longer than 488 nm and wherein isopropylbenzene hydroperoxide is converted into methanol and acetophenone by one pathway and to acetone and phenol by another pathway.

10. A process for preparation of cyclohexanone by a selective photooxidation of cyclohexane, said process comprising the steps:
    (a) preparing a zeolite support matrix by dehydrating a zeolite selected from the group consisting of BaY, NaY and CaY zeolite under vacuum at temperature from about 150° to about 250° C. for about 12 to about 16 hours;
    (b) loading cyclohexane onto the dehydrated zeolite support matrix having an electrostatic field at least 0.2 V/Å;
    (c) introducing oxygen into the matrix of step (b) loaded with cyclohexane under vacuum from about 400 Torr to about 6080 Torr;
    (d) irradiating the matrix of step (c) with a visible light having a wavelength from about 400 to about 550 nm; and (e) selectively generating cyclohexanone as a final product with at least 95% selectivity.

11. The process of claim 10 wherein the zeolite is NaY having the electrostatic field about 0.2 V/Å, wherein the visible light has a wavelength below 500 nm in blue or green emission region, wherein irradiation is performed at room temperature for about three hours.

12. The process of claim 11 wherein the zeolite is BaY, wherein the BaY zeolite has the electrostatic field 0.3 V/Å, the visible light has a wavelength in blue region about 480 nm, oxygen is introduced under pressure about 760 Torr to about 1500 Torr and irradiation is performed at room temperature for about three hours.

13. A process for a selective photooxidation of alkanes, said process comprising the steps:

(a) preparing a zeolite support matrix by dehydrating a zeolite selected from the group consisting of BaY, NaY and CaY zeolite under vacuum at temperature from about 150° to about 250° C. for about 12 to about 16 hours;

(b) loading the alkane in amount about 10 umol onto about a 10 mg pellet of the dehydrated zeolite support matrix having an electrostatic field above 0.2 V/Å, at pressure from 10–1000 Torr;

(c) introducing oxygen into the matrix of step (b) under vacuum from about 400 Torr to about 7600 Torr;

(d) irradiating the matrix of step (c) with a visible light in yellow or red region having a wavelength of about 500 to about 700 nm at temperatures from about −100° to about 30° C. for about one to ten hours; and (e) producing an alkane oxidation product with about at least 80% selectivity.

14. The process of claim 13 wherein the alkane is selected from the group consisting of butane, isobutane, propane, ethane and methane.

15. The process of claim 14 wherein the alkane is isobutane or butane loaded onto dehydrated BaY or CaY zeolite under pressure of about 10 Torr and oxygen pressure is about 760 Torr to about 1500 Torr at 0° C. to room temperature, wherein said zeolite has the electrostatic field above 0.3 V/Å, wherein the irradiation is performed at room temperature for one to ten hours with visible light having a wavelength up to 540 nm, and wherein the oxidation product is t-butylhydroperoxide.

16. The process of claim 15 wherein the oxidation product is formed with selectivity greater than 98% and conversion rate is greater than 70%.

17. The process of claim 16 wherein t-butyl hydroperoxide is extracted from the zeolite matrix by nitrogen stream at temperatures from 50° to 80° C.

18. The process of claim 14 wherein the alkane is propane loaded onto dehydrated BaY or CaY zeolite matrix under pressure of about 150 Torr and oxygen pressure about 760 Torr at 0° C. to room temperature, wherein said zeolite has the electrostatic field above 0.3 V/Å, wherein the irradiation is performed at room temperature for about one to ten hours with a visible blue or green light having a wavelength up to 550 nm, and wherein the oxidation product is propyl hydroperoxide and acetone.

19. The process of claim 14 wherein the alkane is ethane loaded onto dehydrated CaY zeolite matrix under pressure of 300 Torr and oxygen pressure 760–1320 Torr at 0° C. to room temperature, wherein said zeolite has the electrostatic field above 0.3 VÅ, wherein the irradiation is performed at room temperature for one to ten hours with a visible blue or green light having a wavelength up to 550 nm, and wherein the oxidation product is ethyl hydroperoxide and acetaldehyde.

20. The process of claim 14 wherein the alkane is methane loaded onto dehydrated CaY zeolite matrix under pressure of 300 Torr and oxygen pressure about 760 Torr to about 7000 Torr at between 0° C. to room temperature, wherein said zeolite has the electrostatic field above 0.3 V/Å, wherein the irradiation is performed at room temperature for one to ten hours with a visible blue or green light having a wavelength up to 550 nm, and wherein the oxidation product is formaldehyde.

* * * * *